US011699519B1

(12) United States Patent
Roh et al.

(10) Patent No.: US 11,699,519 B1
(45) Date of Patent: Jul. 11, 2023

(54) SYSTEM FOR MAINTAINING AND CONTROLLING SURGICAL TOOLS

(71) Applicant: IX Innovation LLC, Seattle, WA (US)

(72) Inventors: Jeffrey Roh, Seattle, WA (US); Justin Esterberg, Mercer Island, WA (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/568,491

(22) Filed: Jan. 4, 2022

(51) Int. Cl.
*G16H 40/40* (2018.01)
*A61B 34/30* (2016.01)
*A61B 34/00* (2016.01)
*A61B 34/20* (2016.01)

(52) U.S. Cl.
CPC ............. *G16H 40/40* (2018.01); *A61B 34/20* (2016.02); *A61B 34/25* (2016.02); *A61B 34/30* (2016.02); *A61B 2034/2074* (2016.02)

(58) Field of Classification Search
CPC ................................ G16H 40/40; A61B 34/30
See application file for complete search history.

(56) References Cited

U.S. PATENT DOCUMENTS

| | | | |
|---|---|---|---|
| 2009/0306581 A1* | 12/2009 | Claus | A61B 90/20 604/22 |
| 2014/0081659 A1* | 3/2014 | Nawana | A61B 5/4833 705/3 |
| 2016/0253472 A1* | 9/2016 | Pedersen | A61B 5/0013 705/2 |
| 2019/0105118 A1* | 4/2019 | Itkowitz | B25J 9/1689 |
| 2020/0038084 A1* | 2/2020 | Brown | A61B 17/1626 |
| 2020/0273575 A1* | 8/2020 | Wolf | G06V 20/40 |
| 2022/0104806 A1* | 4/2022 | Shelton, IV | A61B 17/0686 |

* cited by examiner

Primary Examiner — Evangeline Barr
(74) Attorney, Agent, or Firm — Perkins Coie LLP

(57) ABSTRACT

Methods, apparatuses, and systems for maintaining and controlling surgical tools are disclosed. For each surgical tool, a surgeon can give verbal commands which can result in feedback provided by a synthesized voice or the execution of an action as instructed by the verbal command. The tools are monitored during use to ensure the tools remain within their operating parameters. The system alerts the surgeon should the tools approach their operational limitations.

19 Claims, 12 Drawing Sheets

| Tool ID | Tool Type | Rotational/Oscillating Speed (RPM) | | | Operating Temperature (°F) | | Maintenance Frequency Grease Bearings |
|---|---|---|---|---|---|---|---|
| | | Minimum | Maximum | Increment | Default | Minimum | Maximum | |
| 2345 | Rotary | 200 | 800 | 100 | 500 | 40 | 140 | Quarterly |
| 5634 | Rotary | 100 | 500 | 50 | 250 | 40 | 140 | Quarterly |
| 6234 | Rotary | 500 | 2000 | 100 | 1000 | 40 | 180 | Monthly |
| 8456 | Oscillating | 200 | 1000 | 200 | 600 | 40 | 150 | Semi-Annually |
| 1274 | Oscillating | 100 | 600 | 50 | 350 | 40 | 140 | Annually |
| 1275 | Rotary | 300 | 900 | 300 | 300 | 40 | 160 | Bi-Monthly |

*FIG. 7*

| Tool ID | Tool Type | Maintenance Event | Date Serviced | Date of Previous Service | Date of Next Servicing | Current Rotational Speed (RPM) |
|---|---|---|---|---|---|---|
| 2345 | Rotary | Grease Bearings | 5/4/2021 | 2/8/2021 | 8/4/2021 | 500 |
| 2345 | Rotary | Replace Switch | 3/12/2021 | N/A | N/A | 500 |
| 2345 | Rotary | Replace Bearings | 6/5/2020 | N/A | 6/5/2025 | 500 |
| 2345 | Rotary | Replace Tool Chuck | 9/24/2020 | N/A | N/A | 500 |
| 2345 | Rotary | Annual Servicing | 9/18/2020 | 8/20/2019 | 9/18/2021 | 500 |
| 5634 | Rotary | Annual Servicing | 6/30/2021 | 5/21/2020 | 6/30/2022 | 300 |
| 5634 | Rotary | Grease Bearings | 4/16/2021 | 1/18/2021 | 7/16/2021 | 300 |
| 5634 | Rotary | Annual Servicing | 5/21/2020 | 5/22/2019 | 6/21/2021 | 300 |

*FIG. 8*

SYSTEM FOR MAINTAINING AND CONTROLLING SURGICAL TOOLS

TECHNICAL FIELD

The present disclosure is generally related to automated and robotic surgical procedures and specifically to systems and methods for maintaining and controlling surgical tools.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure as well as technical surgical errors during the operation. For example, adverse events can occur due to (i) breakdown in communication within and among the surgical team, care providers, patients, and their families; (ii) delay in diagnosis or failure to diagnose; and (iii) delay in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 7 is a table illustrating an example tool parameter database, in accordance with one or more embodiments.

FIG. 8 is a table illustrating an example tool maintenance database, in accordance with one or more embodiments.

DETAILED DESCRIPTION

Figure 1:
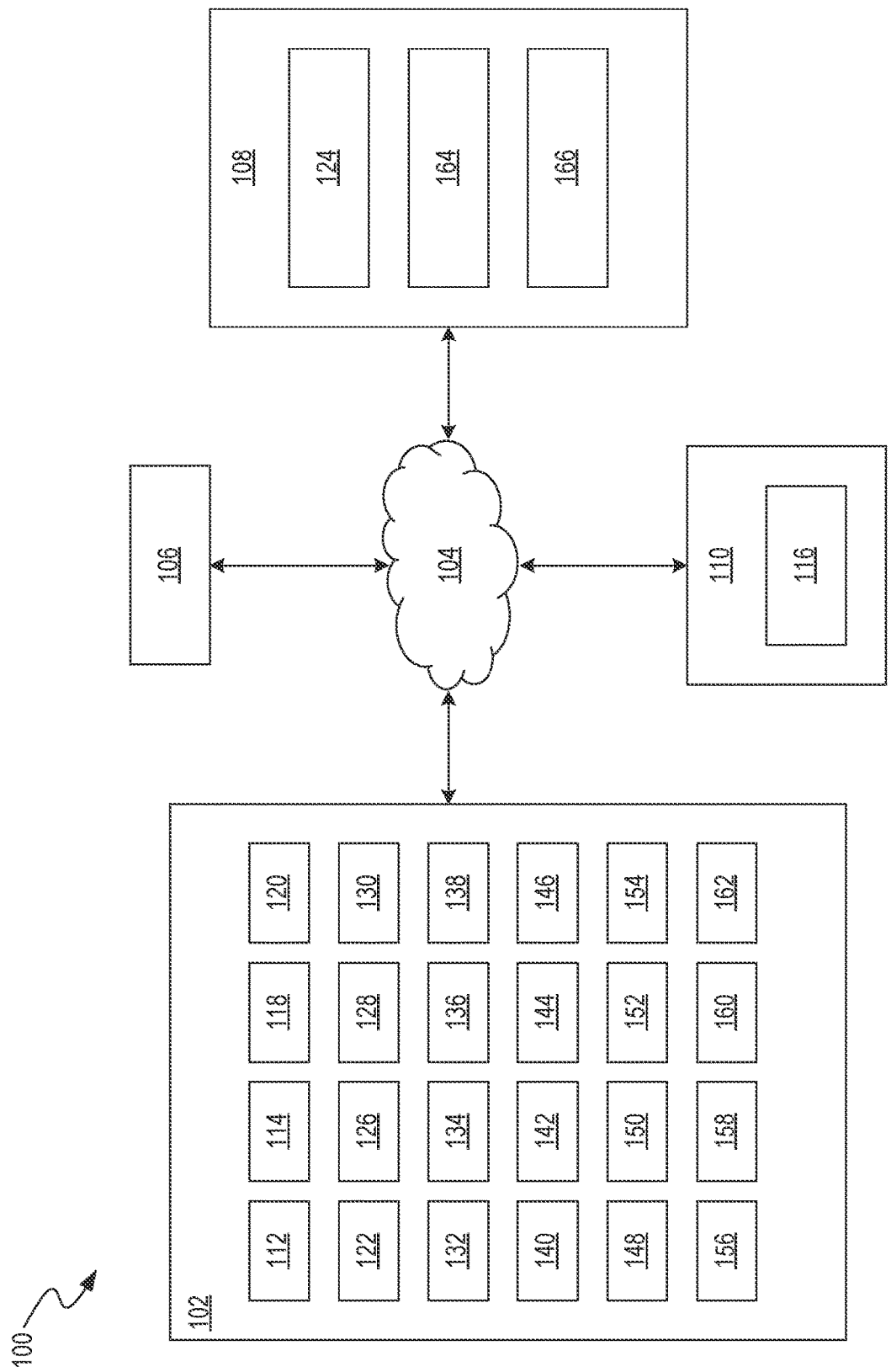
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "602") can implement components, operations, or structures (e.g., "602a") described as a single instance. Further, plural instances (e.g., "602") refer collectively to a set of components, operations, or structures (e.g., "602a") described as a single instance. The description of a single component (e.g., "602a") applies equally to a like-numbered component (e.g., "602b") unless indicated otherwise. These and other aspects, features, and implementations can be expressed as methods, apparatus, systems, components, program products, means or steps for performing a function, and in other ways. These and other aspects, features, and implementations will become apparent from the following descriptions, including the claims.

Surgical tools are used to perform precise actions. Suboptimal functioning, such as lower than needed rotational speed, can result in complications during a surgical procedure. Many surgical tools exist and some surgical tools, such as drills are used in different procedures, despite otherwise being identical. Such tools need to be customized for each procedure. For example, a drill can have a higher maximum rotational speed for one procedure, while another otherwise identical drill can have a lower rotational speed to ensure the patient is not harmed or other surgical implements such as an implant is not damaged during the procedure. Additional tools increase cost and the complexity of tool maintenance and inventory management. Traditionally, a surgeon is trained in the use of a tool prior to its use. However, surgeons still have questions, particularly when using a new tool. Further, a surgeon may wish to have a greater amount of control over their tool, such as limiting the amount of power or the rotational speed of a tool to ensure that harm is not done to the patient.

The embodiments disclosed herein describe methods, apparatuses, and systems for maintaining and controlling surgical tools. In some embodiments, for each surgical tool, a surgeon can give verbal commands, which can result in feedback provided by a synthesized voice or the execution of an action as instructed by the verbal command. The tools are monitored during use to ensure the tools remain within their operating parameters. The system alerts the surgeon should the tools approach their operational limitations.

The advantages and benefits of the methods, systems, and apparatus disclosed herein include compatibility with best practice guidelines for performing surgery in an operating room, e.g., from regulatory bodies and professional standards organizations such as the Association for Surgical Technologists. The robotic surgical system disclosed provides that surgical tools are well maintained to be in an immediate state of readiness. Further, the embodiments disclosed provide methods for performing maintenance and tracking such that a tool remains operational at all times. The disclosed methods provide maintenance according to the manufacturer's instructions and/or maintenance based on the passage of time or tool usage. As such, the disclosed systems provide methods of interacting with and controlling the operational parameters of a surgical tool. In addition, the embodiments disclosed provide that maintenance is performed routinely and prior to use during a surgical procedure. Thus, a tool's reliability increases. Enabling a surgeon to interact with and adjust the configuration of a tool during a procedure—when their hands may be unavailable to interface with the tool—affords the surgeon increased control over the tool. Moreover, the embodiments reduce manual interactions with a physical interface on a tool that can cause the tool to move in a manner which could harm the patient. The resulting tool is more efficient, can be operated more safely, and can provide increased precision.

The robotic surgery technologies disclosed further offer valuable enhancements to medical or surgical processes through improved precision, stability, and dexterity. The disclosed methods relieve medical personnel from routine tasks and make medical procedures safer and less costly for patients. The embodiments disclosed enable more accurate surgery to be performed in more minute locations on or within the human body. The embodiments also address the use of dangerous substances. The adoption of robotic systems, according to the embodiments disclosed herein, provides several additional benefits, including efficiency and speed improvements, lower costs, and higher accuracy. The equipment tracking system integrated into the disclosed embodiments offers flexibility and other advantages, such as requiring no line-of-sight, reading multiple radio frequency identification (RFID) objects at once, and scanning at a distance. The advantages offered by the surgical tower according to the embodiments disclosed herein are smaller incisions, less pain, lower risk of infection, shorter hospital stays, quicker recovery time, less scarring, and reduced blood loss. The advantages of the convolutional neural network (CNN) used for machine learning (ML) in the disclosed embodiments include the obviation of feature extraction and the use of shared weight in convolutional layers, which means that the same filter (weights bank) is used for each node in the layer; this both reduces memory footprint and improves performance.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or outpatient surgery center.

In some embodiments, the system 100 includes one or more medical or surgical patient monitors 112. The monitors 112 can include a vital signs monitor (a medical diagnostic instrument), which can be a portable, battery powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiological parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end tidal CO2 monitor or capnography monitor used for measurement of the level of carbon dioxide that is released at the end of an exhaled breath (referred to as end tidal carbon dioxide, ETCO2). An end tidal CO2 monitor or capnography monitor is widely used in anesthesia and intensive care.

ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end tidal CO2 monitor can be configured as side stream (diverting) or mainstream (non-diverting). A diverting end tidal CO2 monitor transports a portion of a patient's respired gases from the sampling site to the end tidal CO2 monitor while a non-diverting end tidal CO2 monitor does not transport gas away. Also, measurement by the end tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in artery, used in the operating room 102) for measurement. The non-invasive method (referred to as a sphygmomanometer) works by measurement of force exerted against arterial walls during (i) ventricular systole (i.e., systolic blood pressure occurs when the heart beats and pushes blood through the arteries) and (ii) ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate—the rate at which breathing occurs—and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can cause a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia, where the heart rate becomes faster, and bradycardia, where the heart rate becomes slower), coronary heart disease, heart attacks, or cardiomyopathy. The instrument used for measurement of the electrocardiogram is called an electrocardiograph, which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which helps in guiding the surgeon during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP): the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG): the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation Spontaneous EMG is recorded by the insertion of a needle electrode. Triggered EMG refers to the recording of myoelectric signals during stimulation of a target site such as a pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgeon or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by cutting a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. The doctor moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgeon makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals across long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles, which allow the surgeon to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery, which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engage with one another. When a telescope is used to operate on the abdomen, the procedure is called laparoscopy. The surgical tower 128 typically includes access to a variety of surgical tools, such as for electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles), which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels that are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument can 130 consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools thereby minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool-tissue interaction forces. During MIS, the field of view and workspace of surgical tools are compromised due to the indirect access to the anatomy and lack of surgeon's hand-eye coordination. The sensors 134 provide a tactile sensation to the surgeon by providing information regarding shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used can be brain/spinal cord anomalies, tumors in the body, breast cancer screening, joint injuries, uterine/pelvic pain detection, or heart problems. For the creation of the image by an MRI instrument, magnetic resonance is produced by powerful magnets, which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI is more widely suitable for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer, which produces sound waves and sends them into the body. The sound waves that are reflected are converted into electrical signals, which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgeons in the placement of specialized surgical instruments and implants. The patient images are taken to guide the physician before or during the medical procedure. The stereotactic navigation system 138 includes a camera having infrared sensors to determine the location of the tip of the probe being used in the surgical procedure. This information is sent in real-time so that the surgeons have a clear image of the precise location where they are working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a post-operative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table that is designed for use in spinal surgeries and can be used in a variety of spinal procedures in supine, prone, or lateral positions in a safe manner. Two peculiar features of the Jackson table 144 are the absence of central table support and an ability to rotate the table through 180 degrees. The Jackson table 144 is supported at both ends, which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets, which cover the patient. The blanket can be designed to use pressure points on the patient's body to prevent heat from reaching areas at risk for pressure sores or burns. The blanket can also include drainage holes where fluid passes through the surface of the blanket to linen underneath, which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for every-one in the operating room 102 (e.g., surgeon, anesthesiologist, nurses, and patient). Some factors that can contribute to poor quality in the environment of the operating room 102 are temperature, ventilation, and humidity, and those conditions can lead to profound effects on the health and work productivity of people in the operating room 102. As an example: surgeons prefer a cool, dry climate since they work under bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter (HEPA filter). A HEPA filter protects a patient from infection and contamination using a filter, which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system that controls the muscles). A major percentage of orthopedic tools are made of plastic. The orthopedic tools can be divided into the following specialties: hand and wrist, foot and ankle, shoulder, and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be either absorbable (the stitches automatically break down harmlessly in the body over time without intervention) or non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as a sensor/transducer, a signal conditioner, a display, or a data storage unit, etc. In some embodiments, the medical equipment includes a sensor to receive a signal from instruments measuring a patient's body, a transducer for converting one form of energy to electrical energy, a signal conditioner such as an amplifier, filter, etc., to convert the output from the transducer into an electrical value, a display to provide a visual representation of the measured parameter or quantity, or a storage system to store data, which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allow it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor, which generates a continuous stream of pressurized air that travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment. The consumables 158 can include gloves, gowns, masks, syringes, needles, sutures, staples, tubing, catheters, or adhesives for wound dressing, in addition to other surgical tools needed by doctors and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries are performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR are a digital version of patients' paper charts. The EHR database 106 can contain more information than a traditional patient chart, including, but not limited to, a patients' medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected, and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker (e.g., the speaker 632 of FIG. 6), etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

Figure 2:
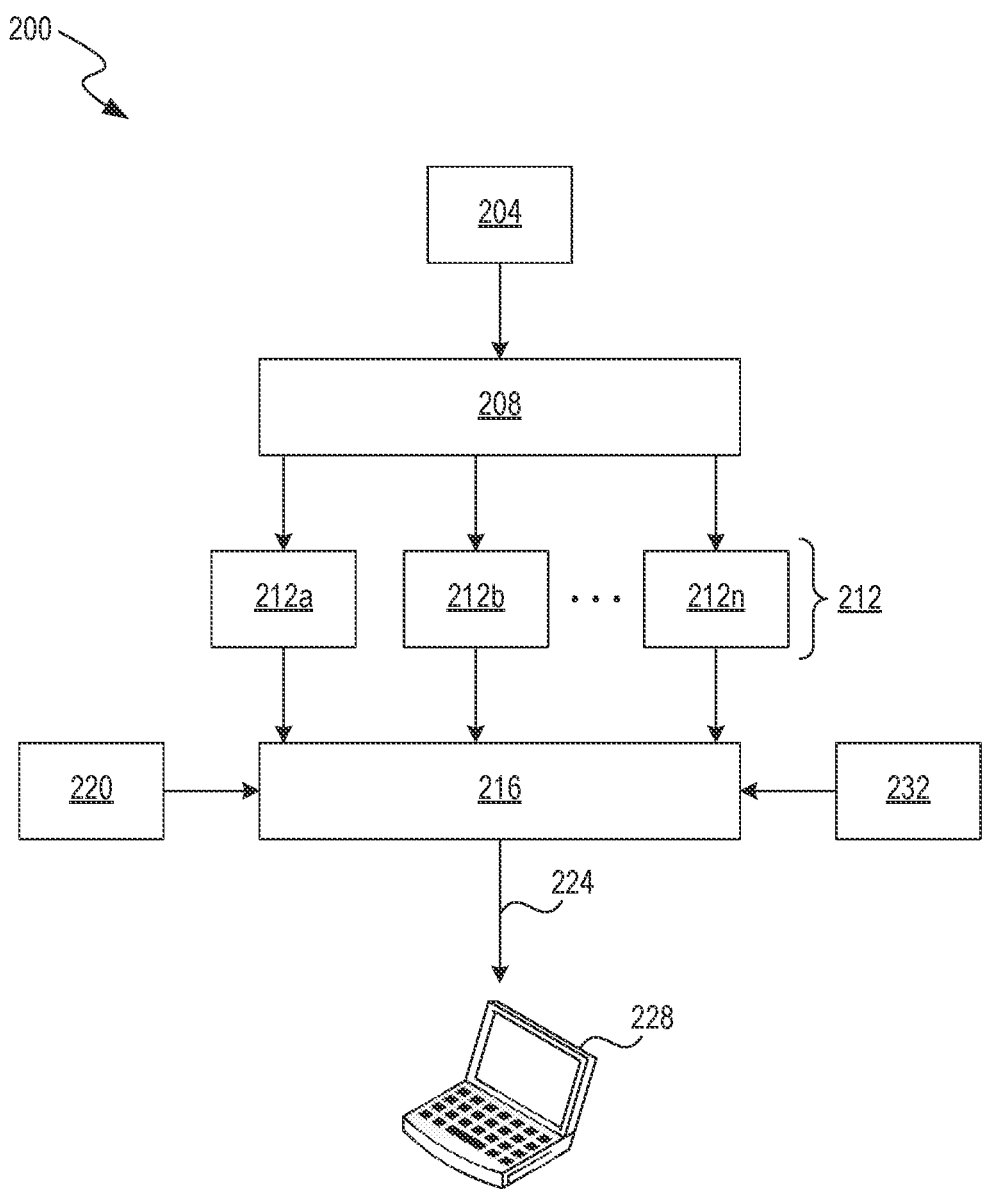
FIG. 2 is a block diagram illustrating an example machine learning (ML) system, in accordance with one or more embodiments.

FIG. 2 is a block diagram illustrating an example machine learning (ML) system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . , 212n. The feature extraction module 208 reduces the redundancy in the input data 204, e.g., repetitive data values, to transform the input data 204 into the reduced set of features 212, e.g., features 212a, 212b, . . . , 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker (e.g., the speaker 632 of FIG. 6), etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place.

Figure 3:
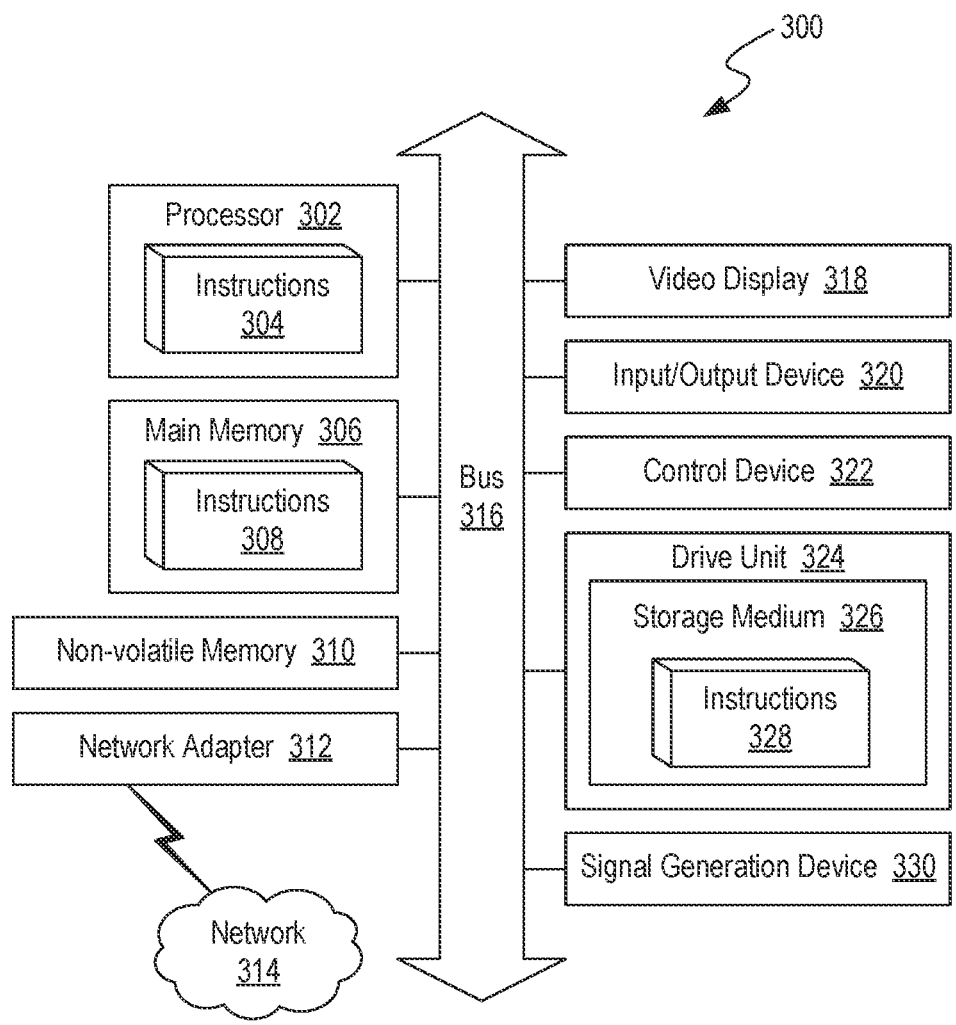
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multilayer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
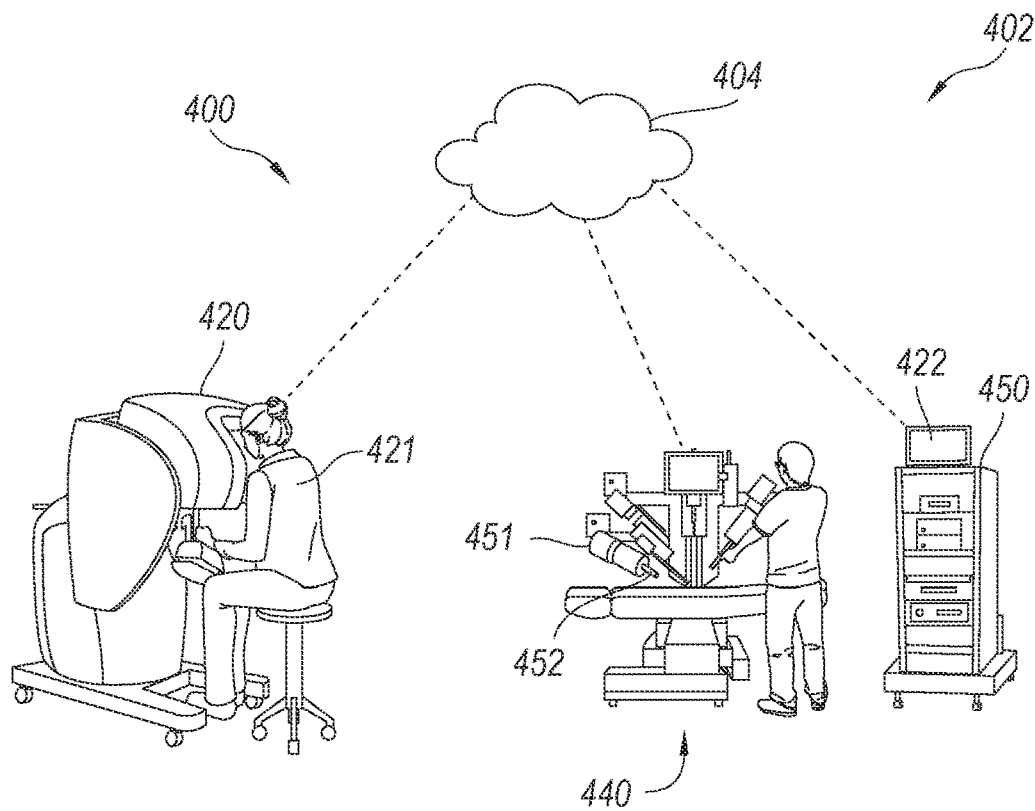
FIG. 4A is a block diagram illustrating an example robotic surgical system, in accordance with one or more embodiments.

FIG. 4A is a block diagram illustrating an example robotic surgical system 400, in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1).

The robotic surgical system 400 includes a user device or console 420 ("console 420"), a surgical robot 440, and a computer or data system 450. The console 420 can be operated by a surgeon and can communicate with components in an operating room 402, remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc. or other features disclosed herein to perform surgical step(s) or procedures or implement steps of processes discussed herein.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to medical images, video, etc. For surgical applications, the images could include, but are not limited to, real-time optical images, real-time ultrasound, real-time OCT images and/or other modalities, or could include pre-operative images, such as MRI, CT, PET, etc. The various imaging modalities can be selectable, programmed, superimposed, and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

Figure 4B:
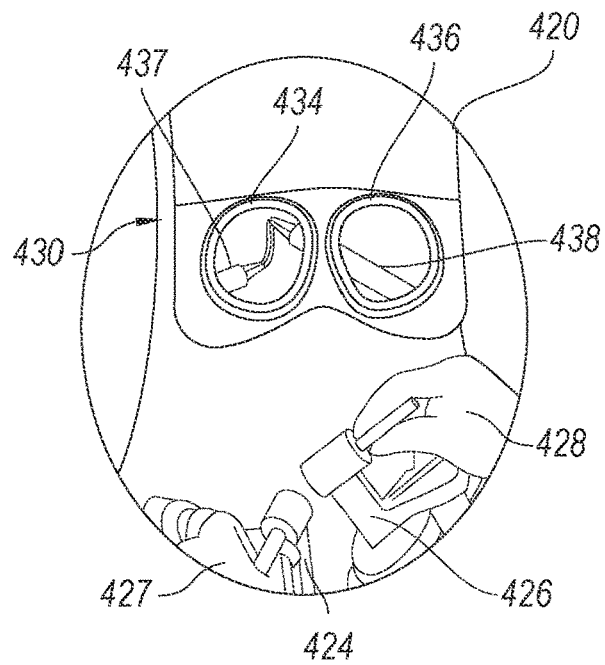
FIG. 4B illustrates an example console of the robotic surgical system of FIG. 4A, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times.

The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452.

In an autonomous mode, the surgical robot 440 can autonomously perform steps under the control of the data system 450. The robotic surgical system 400 can be pre-programmed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include physician input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring. The adverse surgical event can include one or more operating parameters approaching respective critical thresholds, as discussed in connection with FIG. 12. The adverse surgical events can be identified using a machine learning model trained using, for example, prior patient data, training sets (e.g., tool data), etc.

In some embodiments, the robotic surgical system 400 determines whether a detected event (e.g., operational parameters outside a target range or exceeding a threshold, etc.) is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like.

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre-, or post-operative virtual simulations, simulations using models, etc.) can be generated and collected.

The surgical robot 440 can include robotic arms 451 (one identified) with integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein.

The robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, Calif. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modified, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operative or intraoperatively.

Embodiments can provide a means for mapping the surgical path for neurosurgery procedures that minimize damage through artificial intelligence mapping. The software for artificial intelligence is trained to track the least destructive pathway. The physician can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system.

Figure 5:
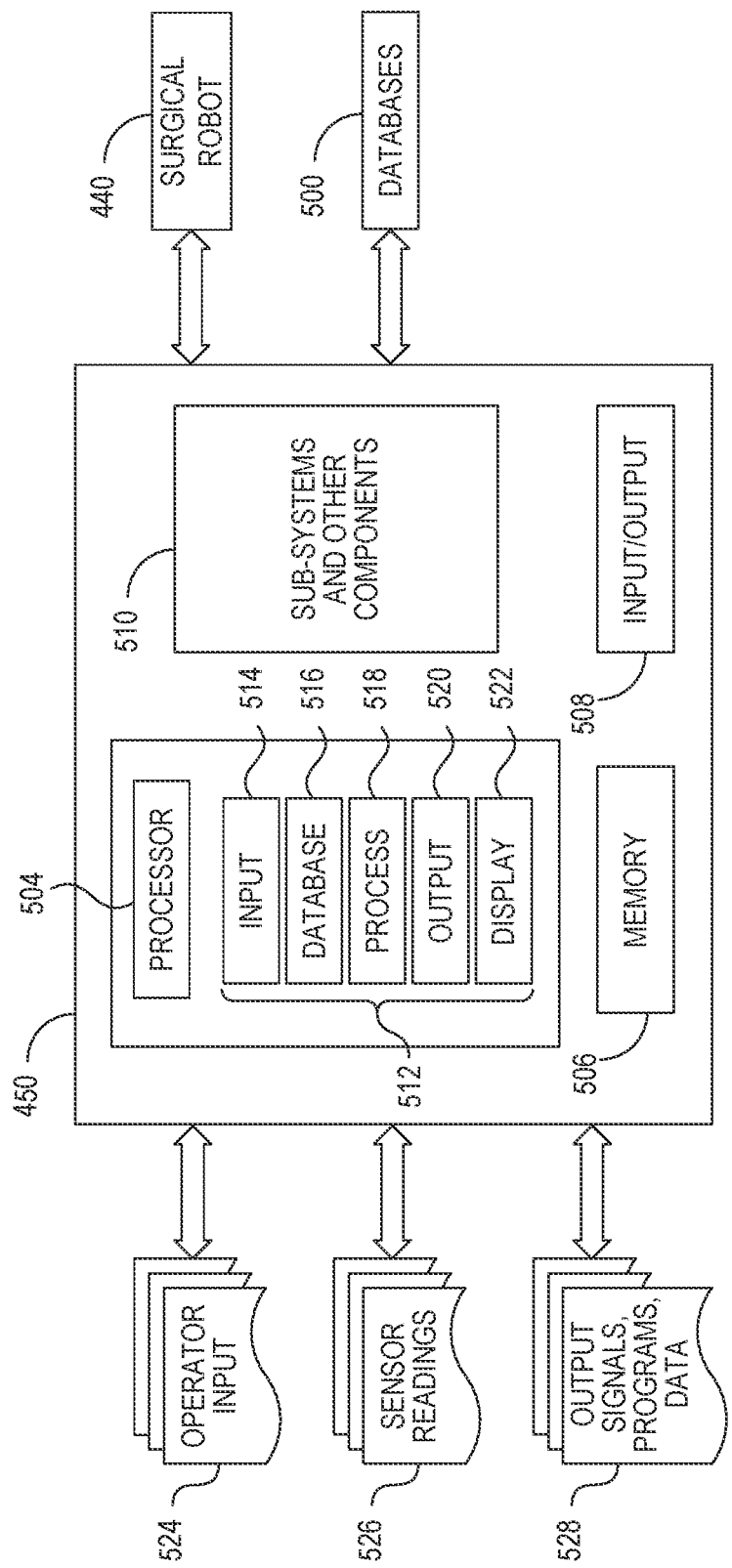
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices, and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field-programmable gate array, or secure application-specific integrated circuit. The memory 506 can store instructions for causing the surgical robot 440 to perform acts disclosed herein.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker (e.g., the speaker 632 of FIG. 6), any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 2600. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between surgical equipment within the surgical room.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

Figure 6:
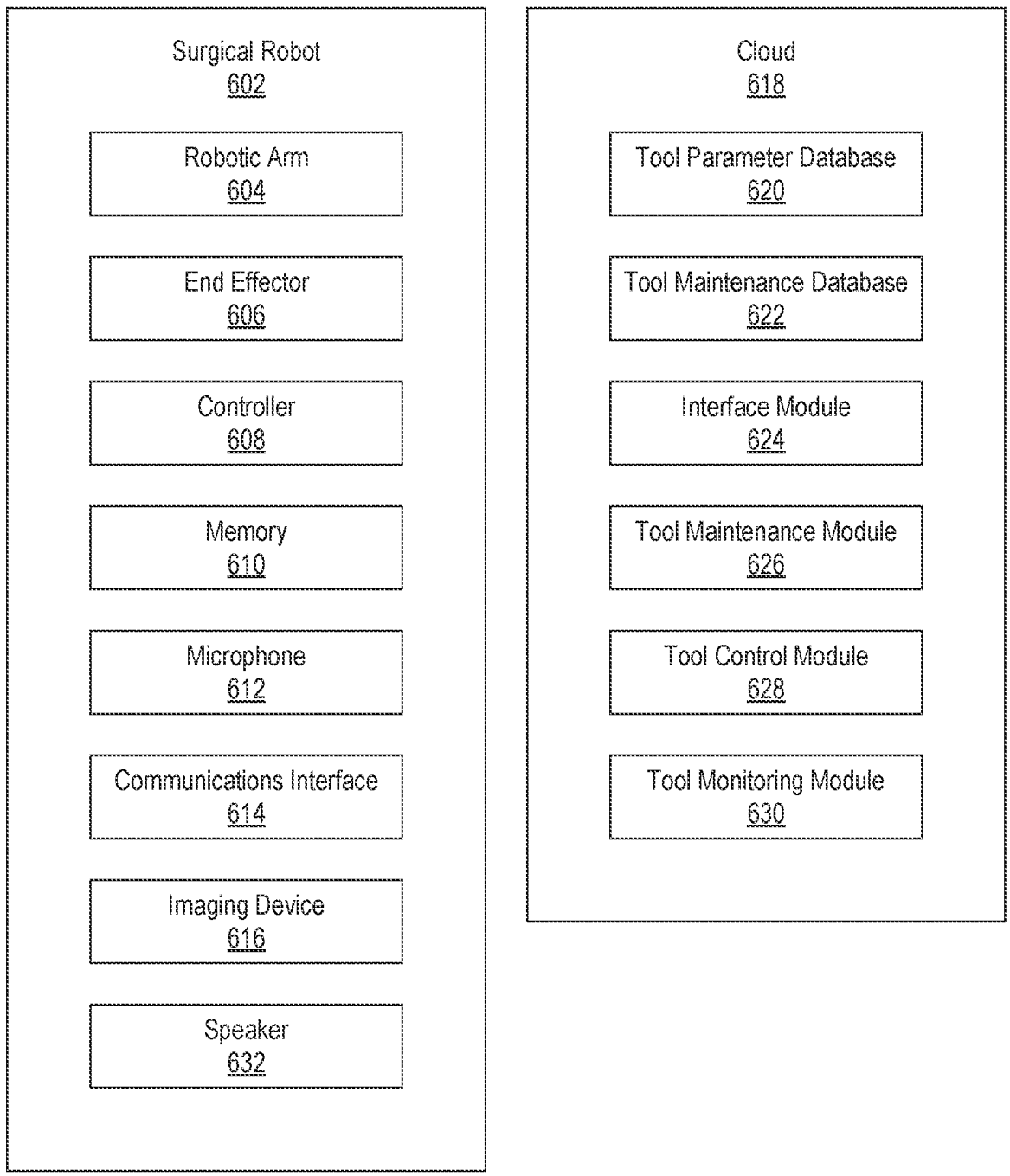
FIG. 6 is a block diagram illustrating an example robotic surgical system for maintaining and controlling surgical tools, in accordance with one or more embodiments.

FIG. 6 is a block diagram illustrating an example robotic surgical system for maintaining and controlling surgical tools, in accordance with one or more embodiments. A robotic "action" refers to one or more physical movements of a surgical robot (e.g., the surgical robot 602), such as aligning a surgical implant component or a surgical tool 154 (see FIG. 1), initiating the rotation of a rotary surgical tool, applying an axial force to a surgical tool 154, etc. The system of FIG. 6 includes the surgical robot 602 and a cloud computing system 618. The system is implemented using the components of the example computer system 300 illustrated and described in more detail with reference to FIG. 3. Likewise, embodiments of the system can include different and/or additional components or can be connected in different ways.

The system of FIG. 6 provides voice control functionality for surgical tools 154 (see FIG. 1). The system comprises the surgical robot 602, which is a robotic system designed to assist a surgeon in performing a surgical operation on a patient. The surgical robot 602 includes at least one controller 608 and at least one robotic arm 604 having at least one end effector 606 or at least one imaging device 616. The surgical robot 602 can further include a user interface for accepting control inputs from a user, such as a surgeon or other medical professional and a communications interface 614 for transmitting and receiving data to and from the cloud 618 for the purpose of training an artificial intelligence (see FIG. 2) operating within the surgical robot 602 or receiving commands from a remote user or an artificial intelligence existing external to the surgical robot 602. The robotic arm 604 is a mechanically actuated arm or lever with at least two degrees of freedom. The robotic arm 604 will typically include the end effector 606 or the imaging device 616 and can include both the end effector 106 and the imaging device 616. The robotic arm 604 can additionally be capable of changing the end effector 606 to facilitate multiple functions and operation of a variety of tools. The robotic arm 604 can be manually controlled or operated in an autonomous or semi-autonomous mode. The surgical robot 602 can have one robotic arm or multiple robotic arms, each of which can be operated independently by one or more users or autonomous systems or a combination of users and autonomous systems.

The system of FIG. 6 can store user profiles that include, without limitation, speech recognition profiles, reference speech input, speech characteristics, user-specific surgical techniques, user preferences, etc. The speech characteristics can include, without limitation, volume, pace, resonance, intonation, pitch, or the like. Acoustic models, language models, pronunciation dictionaries, feature extractors, feature vectors, decoders, word output generators, or the like can be used to recognize speech based on acoustic models, language models, etc.

In some embodiments, a natural language processing model performs natural language processing that includes, without limitation, named entity recognition (e.g., identifying words, phrases, etc.), co-reference resolution, sentiment analysis, tagging (e.g., speech tagging, grammatical tagging, etc.), speech recognition, natural language generation, and/or natural language processing steps. The named entity recognition identifies prompts or phrases commonly used by the surgeon. The system can perform named entity recognition based on captured data (e.g., images captured by cameras) to increase accuracy. For example, the named entity recognition can identify a "tool" of speech input as the tool visible to the surgeon via the monitor console. The system can perform co-reference resolution steps to identify multiple words, such as "tool," "end effector," "instrument," etc., as referring to the same device. Sentiment analysis is used to extract subjective qualities, such as excitement, calmness, or other subjective qualities that may indicate the status of the surgical procedure. Tagging is performed to determine a particular word or string of text based on its use in context. For example, tagging can be used to identify verbs, nouns, etc. For example, if a surgeon states "move the scalpel two inches," tagging can be used to identify the scalpel as a noun and "move" as the verb.

Speech recognition is used for speech-to-text processing to convert speech input into text data. The text data is analyzed using text data processing techniques. In some embodiments, natural language processing includes word sense disambiguation to determine the meaning of a word or phrase having multiple meanings through a process of, for example, semantic analysis. The surgical plan, anatomical data, and other information can be used in combination with speech processing techniques to perform word sense disambiguation. The cloud 618 discussed herein can store databases for surgical techniques to perform word sense disambiguation comparisons.

In some embodiments, the system can identify a user associated with the speech input and can determine whether the user is authorized to control the robotic system. In response to determining that the user is authorized, the system can generate one or more actions to be performed by the robot as discussed below. The modules in the cloud 618 can analyze user profiles for each of the surgical team members to perform user identification, authorization, etc. The modules in the cloud 618 can be trained using preoperative and intraoperative speech training based on the surgical plan, obtained anatomical data, or the like.

The modules in the cloud 618 can be used in telesurgery applications by, for example, receiving speech input from a physician at a remote location. A remote physician can provide speech input via a telephone connected to a computer, network device, smartphone, tablet, or other speech input device. This allows a physician to control at least a portion of telesurgery procedures using speech input while viewing the procedure on a remote computing device. Advantageously, physicians can control surgical procedures without having access to joysticks or other robotic-specific inputs. In some procedures, a physician at the operating room can control a portion of a surgical procedure and a remote physician can control another portion of the surgical procedure. This allows coordination between local and remote physicians. In some procedures, the surgery module 622 can receive input from both physicians and determine which input controls the instruments of the robotic surgery system. To increase accuracy, the modules in the cloud 618 can use a user-specific speech processing module for each physician. The user-specific speech processing module can be trained pre-operatively using speech input from each physician.

The end effector 606 is the end of the robotic arm 604 that performs actions. The end effector 606 is typically a tool or device for interacting with a physical object and can be a surgical tool intended for acting upon or within a patient or can be a gripping device for securing a separate surgical tool to the robotic arm 604. The end effector 606 can be permanently affixed to the end of the robotic arm 604 or can be detachable allowing for a system of interchangeable end effectors which can alternatively be selected and swapped by a single robotic arm or multiple robotic arms. The end effector 606 can include features such as lights or other illumination devices, surgical tools, imaging devices 616, etc. The controller 608 is a logic device or processor for preforming a series of logic operations. Traditionally, the controller 608 is comprised of transistors arranged on a silicon substrate, although the controller 608 can be comprised of any materials and substrates which form a logic circuit. Common logic circuit elements include OR gates, AND gates, XOR gates, NOR gates, NAND gates, etc. The controller 608 can be a microcontroller or a central processing unit (CPU) in a computer. Similarly, a graphical processing unit (GPU) can be used as a controller. The controller 608 can additionally be comprised by the logic element of a quantum computer. The controller 608 uses logic operations to perform computations and can be in communication with the memory 610, for storing data, and a communications interface 614, for sending and receiving data to and from other controllers or devices.

The memory 610 is a medium for storing data. The memory 610 can be volatile memory, such as random-access memory (RAM) which is a cache used by the controller 608 for temporary storage of data for use in computations or persistent memory, such as solid-state drive (SSD), hard disk drive (HDD) or other storage devices including tape drives, flash drives, memory cards, optical drives such as compact disk (CD), digital video disk (DVD), or Blu-ray disc, or data storage on nontraditional mediums. The microphone 612 is a device which converts sound waves into an analog or digital signal. Most commonly, the microphone 612 uses a diaphragm, or physical surface which is caused to oscillate when contacted by sound waves. The microphone 612 can additionally have a diaphragm of varying size. The microphone 612 can include any of the types, liquid microphones, carbon microphones, fiber optic microphones, dynamic microphones, electret microphones, ribbon microphones, laser microphones, condenser microphones, and crystal microphones. The microphone 612 can be omnidirectional, or can be directional, having a cardioid pickup pattern. The directionality can be increased with a super cardioid or hyper cardioid pickup pattern and can similarly include a combination of directionality as with bidirectional microphones.

The communications interface 614, also known as a network interface, is an interface for a device or controller 604 to communicate with another device, controller 608 or network resource such as a cloud server or drive. The communications interface 614 can be wired, such as ethernet cables or universal serial bus (USB) cables, or wireless as in Wi-Fi, Bluetooth, near field communications (NFC), 4G long-term evolution (LTE), 5G, etc. The imaging device 616 is any device capable of detecting sound or electromagnetic waves and assembling a visual representation of the detected waves. Imaging devices 616 can collect waves from any part of the electromagnetic spectrum or sounds at any range of frequencies, often as a matrix of independently acquired measurements which each represent a pixel of a two or three-dimensional image. These measurements can be taken simultaneously or in series via a scanning process or a combination of methods. Some pixels of an image produced by an imaging device can be interpolated from direct measurements representing adjacent pixels in order to increase the resolution of a generated image. The cloud 618 is a distributed network of computers comprising servers and databases. The cloud 618 can be a private cloud, where access is restricted by isolating the network such as preventing external access, or by using encryption to limit access to only authorized users. Alternatively, the cloud 618 can be a public cloud where access is widely available via the internet. A public cloud may not be secured or may include limited security features.

In some embodiments, one or more processors of the surgical system of FIG. 6 configure a subset of surgical tools 154 with parameters for performing a surgical procedure. For example, the tool parameter database 620 stores information about a tool such as its features, limitations, operational ranges, and which of these parameters can be adjusted via manual configuration or via interaction with a tool configuration assistant. The tool parameters are sometimes referred to as "operating parameters." The tool configuration assistant includes a user interface, which can be a keyboard and mouse, touchscreen, or in preferred embodiments, an audio interface enabling a verbal conversation using natural language processing and a synthesized voice to provide input to the surgical robot 602 and receive audio feedback from (e.g., a smart speaker of) the surgical robot 602. The tool parameter database 620 can be populated or maintained in part or its entirety by a third party such as a tool manufacturer. Alternatively, the tool parameter database 620 can access third party resources which may be located on the cloud 618. The tool parameter database 620 can additionally store information regarding the type of maintenance, frequency and procedures which are recommended by the tool manufacturer. The tool maintenance database 622 stores information about tool maintenance schedules including both scheduled and completed maintenance. The tool maintenance database 622 further comprises the maintenance history, including issues found, corrected, and persons responsible for maintenance. The tool maintenance database 622 can also include procedures for maintenance which may differ from manufacturer defined procedures which can be stored in the tool parameter database 620. These differences can be due to the frequency or manner of use.

In some embodiments, one or more processors of the surgical system of FIG. 6 receive a surgical plan for a surgical procedure. For example, the interface module 624 uses the surgical plan to identify available tools from the tool parameter database 620 and further uses the tool maintenance module 626 to verify that each tool is properly maintained. Similarly, the interface module 624 uses the tool control module 628 to configure the tool within the parameters specified in the tool parameter database 620 and further uses the tool monitoring module 630 to monitor the tool during use by using sensors to take measurements and compare them to the tool's operating parameters as stored in the tool parameter database 620. The tool maintenance module 626 receives information describing a selected tool from the interface 624 module and queries the tool parameter database 620 and the tool maintenance database 612 to determine whether maintenance is required to be performed on the selected tool and performing maintenance tasks as determined necessary.

In some embodiments, the surgical system of FIG. 6 determines a surgical step to be performed by the surgical robot 602. Determining the surgical step is performed using a machine learning model (see FIG. 2) based on instructions received from a surgeon. For example, the tool control module 628 receives information describing a selected tool from the interface module 624 and receives inputs from a user and provides feedback to the user or performs an action in response to the user's instructions, such as adjusting the configuration of a tool. The tool control module 628 uses the tool parameter database 620 to verify that the provided instruction received from the user is within the operating parameters of the tool. In some embodiments, one or more sensors (see FIG. 1) monitor a subset of the surgical tools 154 during a surgical procedure. For example, the tool monitoring module 630 receives information describing a selected tool from the interface module 624 and monitors at least on sensor located on the tool for measurements and compares the measurements to the operating range for the tool retrieved from the tool parameter database 620. In some embodiments, one or more processors of the surgical system of FIG. 6 generate an alert responsive to determining that at least one parameter of a subset of the surgical tools 154 is approaching a threshold based on the parameters in the parameter database 620. For example, if a sensor measurement approaches a critical threshold, the user is alerted and informed that the tool can soon exceed its operational parameters. The tool monitoring module 630 further updates the tool maintenance database 622 with the tool usage event as well as any issues reported by the user. FIG. 7 is a table illustrating an example tool parameter database 620, in accordance with one or more embodiments. The tool parameter database 620 is illustrated and described in more detail with reference to FIG. 6. The tool parameter database 620 stores information about tools including their features, limitations, operational ranges, and which of these parameters can be adjusted via manual configuration or by the tool control module 628. The tool parameter database 620 can be populated or maintained in part or its entirety by a third party such as a tool manufacturer. Alternatively, the tool parameter database 620 can access third party resources which can be located on the cloud 618. The tool parameter database 620 can additionally store information regarding the type of maintenance, frequency and procedures which are recommended by the tool manufacturer. The tool parameter database 620 is used by the interface module 624, tool maintenance module 626, tool control module 628, and the tool monitoring module.

FIG. 8 is a table illustrating an example tool maintenance database 622, in accordance with one or more embodiments. The tool maintenance database 622 is illustrated and described in more detail with reference to FIG. 6. The tool maintenance database 622 stores information about tool maintenance schedules including both scheduled and completed maintenance. The tool maintenance database 622 further comprising the maintenance history, including issues found, corrected, and persons responsible for maintenance. The tool maintenance database 622 can also include procedures for maintenance which may differ from manufacturer defined procedures which can be stored in the tool parameter database 620. These differences can be due to the frequency or manner of use. The tool maintenance database 622 additionally stores tool usage information and can also store tool configuration settings. The tool maintenance database 622 can be populated by tool manufacturers, owners, user, etc. The tool maintenance database 622 is additionally populated by the tool maintenance module 626 and the tool monitoring module 630. The tool maintenance database 622 is used by the tool maintenance module 626.

Figure 9:
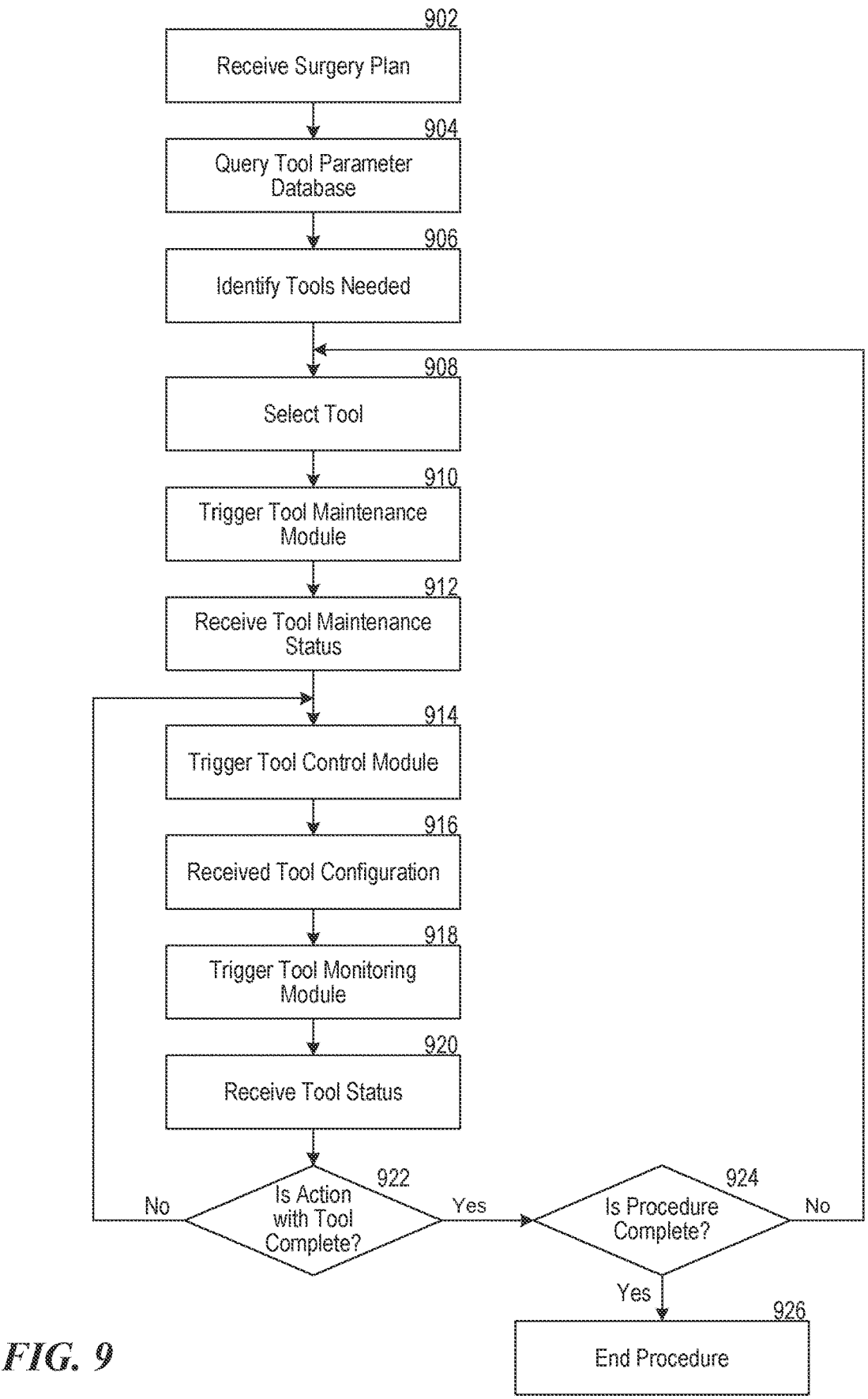
FIG. 9 is a flow diagram illustrating an example process for maintaining and controlling surgical tools, in accordance with one or more embodiments.

FIG. 9 is a flow diagram illustrating an example process for maintaining and controlling surgical tools, in accordance with one or more embodiments. In some embodiments, the process of FIG. 9 is performed by the interface module 624. The interface module 624 is illustrated and described in more detail with reference to FIG. 6. In other embodiments, the process of FIG. 9 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 902, the interface module 624 receives a surgical plan (see FIGS. 4A-5) from a surgeon or via the automated surgical robot 602. If the surgical plan is generated by the automated surgical robot 602, it can be approved by a surgeon prior to use. The surgical plan comprising a series of steps or actions to be taken and can additionally include the tools and materials required for each action. Each step of the surgical plan can further comprise a tool path and tool parameters for executing each step. The tool parameters can be the default settings for the tool or can be selected as the optimal settings for the given operation. The tools selected may not consider the available inventory of tools or their maintenance status. For example, a surgical plan is received for an appendectomy.

In some embodiments, one or more processors of the surgical system of FIG. 6 identify surgical tools from a parameter database based on parameters in the parameter database corresponding to a surgical plan. The parameter database stores maintenance requirements for the surgical tools. For example, in step 904, the interface module 624 queries the tool parameter database 620 for an inventory of available tools. The tools can be immediately available or can have an associated lead time, such as if they are ordered from a vendor or if they are currently undergoing maintenance or are currently in use or scheduled for use in another procedure. The tool parameter database 620 further including operational parameters such as the operating range of rotational speeds for rotary tools, oscillating frequency and distance for oscillating tools, and gripping force for tools such as forceps.

In step 906, the interface module 624 identifies the tools required to execute the surgical plan based upon the tools available according to the tool parameter database 620. If a tool, as can be indicated by the surgical plan, is unavailable according to the tool parameter database 620, an alternate tool is chosen. For example, a rotary tool from Brand A with an operating range of 200-600 revolutions per minute is specified in the surgical plan but is unavailable according to the tool parameter database 620. However, a rotary tool from Brand B with an operating range of 200-800 revolutions per minute is available. The interface module 624 enables substitution of the rotary tool from Brand B for the rotary tool from Brand A.

In step 908, the interface module 624 selects a tool from the tools identified as necessary to execute the surgical plan. For example, a selected tool is a rotary tool with an operating range of 200-800 revolutions per minute. In step 910, the interface module 624 prompts or triggers the tool maintenance module 622 to determine whether maintenance must be performed on the tool prior to its use according to the surgical plan. The tool maintenance module 622 identifies required maintenance tasks, enables the performance of any necessary maintenance, and returns a maintenance status to the interface module 624. For example, maintenance of the selected rotary tool is enabled.

In step 912, the interface module 624 receives a maintenance status of the selected tool. A tool is determined to be ready for use if all necessary maintenance or repairs has been completed. A tool requires maintenance if additional repairs or maintenance tasks must be completed prior to the planned procedure. In some embodiments, a replacement tool can be required if the selected tool requires maintenance, in which case another tool must be selected from the tool parameter database 620. In some embodiments, the microphone 612 receives instructions from a user of the surgical system. The surgical robot 602 adjusts its performing of the surgical procedure by controlling a subset of the surgical tools 154 based on the instructions. For example, in step 914, the interface module 624 prompts or triggers the tool control module 628 to receive instructions from a user in order to configure or control the tool. The user preferably provides instructions via a verbal interface which receives and interprets the user's instructions via natural language processing. The surgical robot 602 can further provide verbal feedback via a synthesized voice in a conversational format. For example, a rotary tool is configured with an operating range of 200-800 revolutions per minute.

In step 916, the interface module 624 receives information describing a configured tool from the tool control module 628. The tool has at least one setting changed via instructions provided by the user, such as minimum, maximum or target movement speed, rotational speed, force, etc. In an example, a rotary tool is being configured to operate at a rotational speed of 500 revolutions per minute. In step 918, the interface module 624 prompts or triggers the tool monitoring module 630 which monitors at least one sensor affixed to, integrated into, or oriented towards the tool and monitors at least one operational parameter of the tool. The tool monitoring module 630 retrieves a warning threshold and a critical threshold from the tool parameter database 620 and provides an alert to the user if the critical threshold is reached or alternatively approached. In an example, the interface module 624 monitors the usage of a rotary tool with an operating range of 200-800 revolutions per minute which has been configured to operate at 500 revolutions per minute.

In some embodiments, one or more processors of the surgical system of FIG. 6 determine that the surgical procedure is complete responsive to determining that a tool status of at least one surgical tool indicates that the at least one surgical tool is idle. For example, in step 920, the interface module 624 receives a tool status from the tool monitoring module. The tool status can be "in nominal," "not in use," "out of service," etc. In an example, the tool status for the selected rotary tool is "not in use." In step 922, the interface module 624 determines whether the action for the tool is complete. The action for the tool is complete if the tool status is "not in use." Alternatively, the action for the tool can be considered complete if the tool's status is "out of service," because the tool can no longer be used, and a replacement may need to be selected. In an example, the tool status is not in use as the action was completed. In step 924, the interface module 624 determines whether the procedure is complete. The procedure is determined to be complete if no steps remain in the surgical plan.

In some embodiments, one or more processors of the surgical system of FIG. 6 determine that the surgical procedure is complete responsive to determining that a subset of the surgical tools 154 has been removed from a patient's body based on images received from at least one imaging device 616 (see FIG. 6). For example, the procedure is determined complete if all surgical tools have been removed from the patient's body and any incisions made in the patient's body have been closed. In an example, a screw has been inserted into a patient using the selected rotary tool, however the procedure is not determined complete as additional implant components remain to be installed. Additionally, the surgical site remains exposed, held open by surgical tools such as a spreader, dilator, or tool channel. In some embodiments, the surgical system of FIG. 6 identifies absence of the surgical tools 154 in the patient's body using a machine learning model (see FIG. 2) based on the images. For example, in step 926, the interface module 624 terminates the session when no steps remain in the surgical plan, all tools have been removed from the patient, and all incisions made in the patient have been closed.

Figure 10:
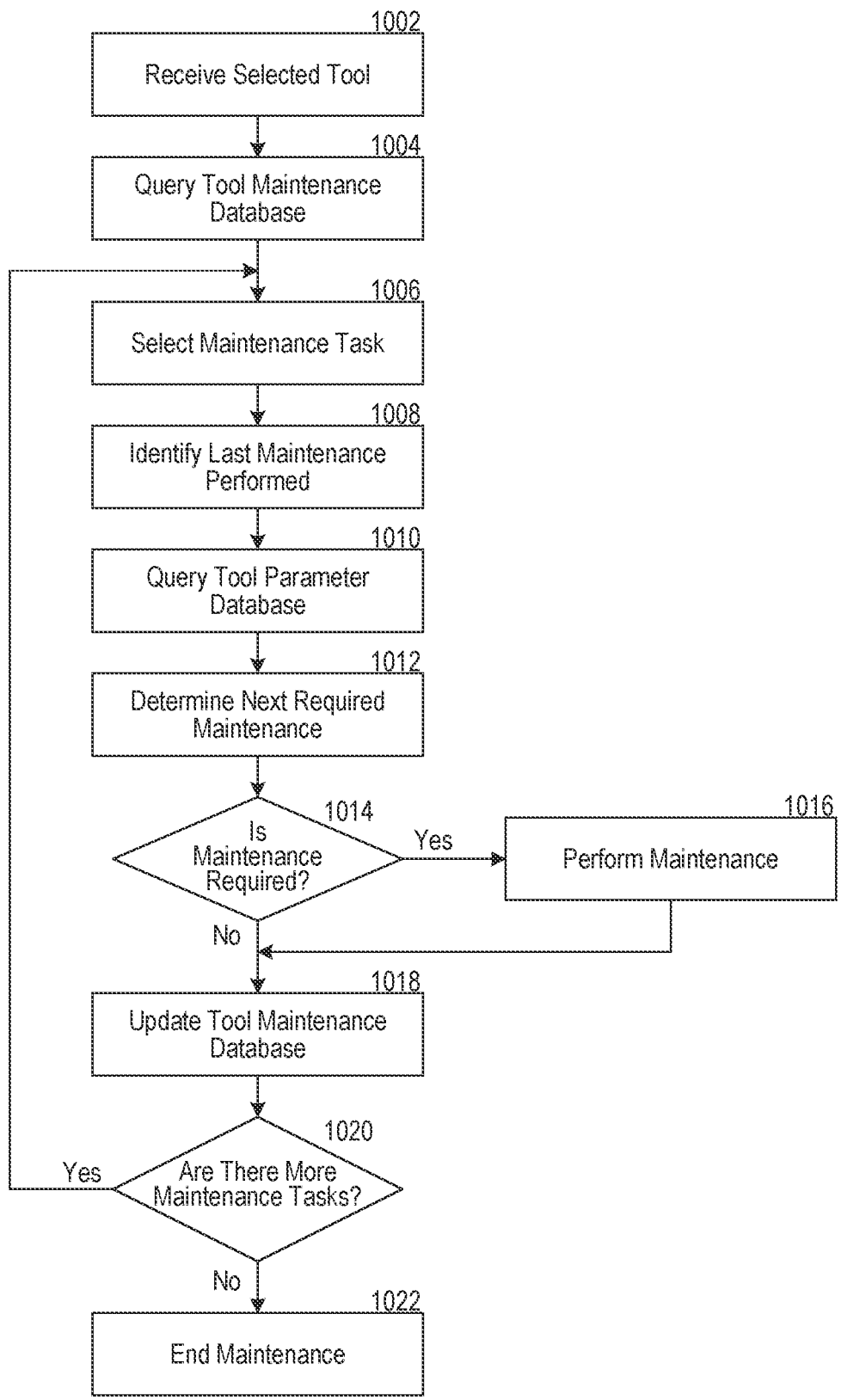
FIG. 10 is a flow diagram illustrating an example process for maintaining and controlling surgical tools, in accordance with one or more embodiments.

FIG. 10 is a flow diagram illustrating an example process for maintaining and controlling surgical tools, in accordance with one or more embodiments. In some embodiments, the process of FIG. 10 is performed by the tool maintenance module 626. The tool maintenance module 626 is illustrated and described in more detail with reference to FIG. 6. In other embodiments, the process of FIG. 10 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In some embodiments, one or more processors of the surgical system of FIG. 6 determine a subset of surgical tools based on a maintenance status of the subset of the surgical tools retrieved from the maintenance database 622. The maintenance database 622 stores maintenance history of the surgical tools. For example, in step 1002, the tool maintenance module 626 receives information describing a tool from the interface module 624. In an example, the selected tool is a rotary tool with an operating range of 200-800 revolutions per minute. In some embodiments, one or more processors of the surgical system of FIG. 6 query the maintenance database 622 to determine that at least one surgical tool of a subset of the surgical tools 154 requires maintenance. For example, in step 1004, the tool maintenance module 626 queries the tool maintenance database 622 for the tool's maintenance records. The maintenance records can include the dates of maintenance activities, the types of maintenance completed and the reason the maintenance was completed such as whether the maintenance activity was regularly scheduled maintenance or was in response to an issue. The maintenance records can additionally include the date of the next scheduled maintenance which can be based upon the manufacturer's recommendations or on procedures established for the hospital or operating room where the tool is being used. Alternatively, a third party can be responsible for maintaining the selected tool and storing the records.

In step 1006, the tool maintenance module 626 selects a maintenance task to be completed on the tool. The maintenance can be a regularly scheduled maintenance activity, such as cleaning and greasing bearings in a rotary tool or can be an emergency repair in response to a reported issue such as a seized bearing or a broken switch. In an example, the selected maintenance task is greasing the bearings in a rotary tool. In step 1008, the tool maintenance module 626 identifies when the selected maintenance task was performed. In an example, the bearings in a rotary tool were greased on May 4, 2021.

In step 1010, the tool maintenance module 626 queries the tool parameter database 620 for the manufacturer's recommended maintenance frequency for the selected maintenance task. The recommended maintenance frequency can be related to usage, such as after a specified number of procedures or a number of hours. Alternatively, the maintenance frequency can be related to a period of elapsed time, such as after a period of weeks, months or years has elapsed. In an example, the bearings of the rotary tool must be greased after 10 hours of usage. Alternatively, the bearings of the rotary tool should be greased every three months. In step 1012, the tool maintenance module 626 determines the next required maintenance event for the selected tool and maintenance task. The next maintenance event can be based upon the manufacturer's recommended maintenance frequency or can alternatively be based upon a procedure for the hospital or operating room using the tool or alternatively a third party responsible for maintaining the selected tool. If different than the manufacturer's recommendation, the maintenance frequency can be more frequent or less frequent. In an example, the maintenance frequency for greasing the bearings of the rotary tool is every three months. Because the last time this maintenance task was required was May 4, 2021, the next maintenance date is Aug. 4, 2021.

In step 1014, the tool maintenance module 626 determines whether maintenance is required. Maintenance may be required if the next maintenance date for the selected maintenance task has elapsed or will have elapsed by the date during which the selected tool is to be used in a procedure. Alternatively, maintenance may be required if an issue has been reported regarding the tool, such as the bearings freezing preventing the rotary tool from spinning freely. In an example, the maintenance frequency for greasing the bearings of the rotary tool is every three months. Because fewer than three months have elapsed from the present day, Jul. 2, 2021, to the last maintenance date of May 4, 2021, maintenance is not required.

In some embodiments, one or more processors of the surgical system of FIG. 6 enable maintenance to be performed on at least one surgical tool to achieve a maintenance status using the parameters in the parameter database 620. For example, in step 1016, the tool maintenance module 626 enables a selected maintenance task to be performed if the next maintenance date for the selected maintenance task has elapsed or will have elapsed by the date during which the selected tool is to be used in a procedure. Alternatively, the tool maintenance module 626 enables performance of maintenance if an issue has been reported regarding the tool, such as the bearings freezing preventing the rotary tool from spinning freely. In an example, a robot or robotic device performs a maintenance task of greasing the bearings of the rotary tool by disassembling the tool to gain access to the bearings and applying grease to the bearings. The task of greasing the bearings can additionally require any previously applied grease to be removed along with any dirt, debris or contaminants which can be present prior to applying new grease to the bearings. Finally, the robot or robotic device reassembles and tests the rotary tool to ensure the tool is fully operational.

In step 1018, the tool maintenance module 626 updates the tool maintenance database 622 with the maintenance event performed. If no maintenance task was performed, the tool maintenance module 626 updates the next maintenance date. The tool maintenance database 622 can additionally be updated with the scheduled usage of the tool, particularly if the tool's usage can be a determinant in the next maintenance date. In some embodiments, the tool's next maintenance event can be affected by usage, such as requiring maintenance more frequently than normally recommended if used more than a specified number of times or cumulative number of times. For example, a tool can require a maintenance task every three months, however it can be required sooner if 10 hours of cumulative use have accrued before three months has passed since the last maintenance date. In an example, the tool maintenance module 626 updates the tool maintenance database 622 that the rotary tool's bearings were greased and stores the date the maintenance was performed as Jul. 2, 2021.

In step 1020, the tool maintenance module 626 determines whether there are any more maintenance tasks which may need to be performed on the selected tool. In an example, the rotary tool must additionally be sterilized before or after each use. In an alternate example, the rotary tool is pneumatically operated and must be pressure tested for leaks once every year. In a further example, the rotary tool must have the switches serviced at least once every year to ensure that they operate reliably. In step 1022, the tool maintenance module 626 terminates the maintenance session on the tool and provides or returns the tool's maintenance status to the interface module 126. The tool's maintenance status may be ready for use, or alternatively maintenance required.

Figure 11:
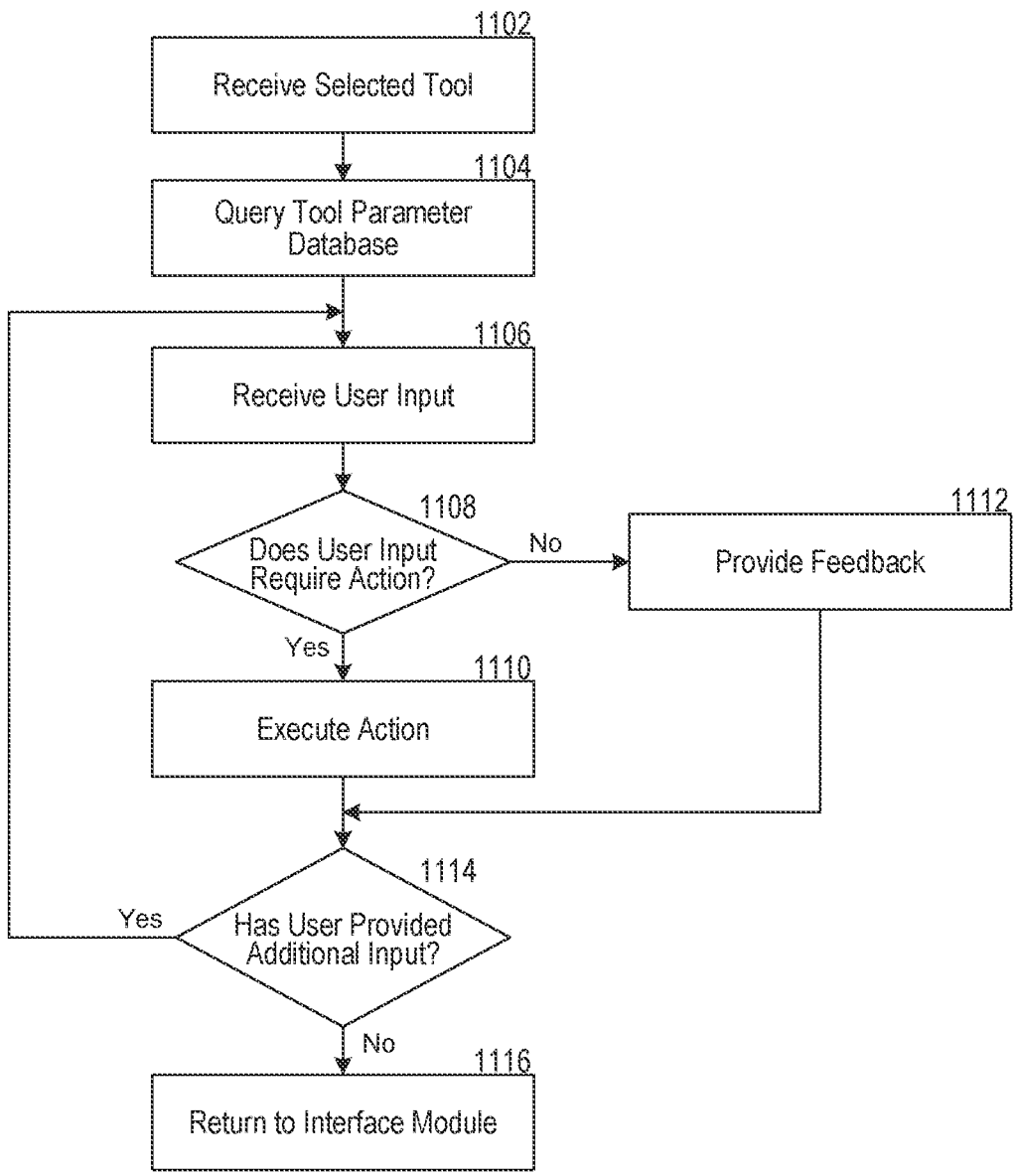
FIG. 11 is a flow diagram illustrating an example process for maintaining and controlling surgical tools, in accordance with one or more embodiments.

FIG. 11 is a flow diagram illustrating an example process for maintaining and controlling surgical tools, in accordance with one or more embodiments. In some embodiments, the process of FIG. 11 is performed by the tool control module 628. The tool control module 628 is illustrated and described in more detail with reference to FIG. 6. In other embodiments, the process of FIG. 11 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1102, the tool control module 628 receives information describing a tool from the interface module 624. In an example, the selected tool is a rotary tool with an operating range of 200-800 revolutions per minute. In step 1104, the tool control module 628 queries the tool parameter database 620 for the tool's operational parameters as specified by the manufacturer. Alternatively, the operational parameters may have been adjusted or otherwise set by the hospital or operating room where the tool is to be used or alternatively a third party who can be responsible for maintenance of the tool. The tool parameters can include minimum and maximum values, such as movement speed, rotational speed, or forces such as gripping, spreading, pushing, or pulling forces. Similarly, the tool parameters can include an increment value in addition to the minimum and maximum values. For example, a tool can have a minimum rotational speed of 200 revolutions per minute and a maximum rotational speed of 800 revolutions per minute with an increment of 100 revolutions per minute such that 200, 300, 400, 500, 600, 700, and 800 revolutions per minute are all valid tool parameters while values such as 550, 473, or 609, etc., are invalid tool parameters.

In step 1106, the tool control module 628 receives a user input. The user input can be provided via a physical user interface such as a touchscreen, keyboard and mouse, joystick, etc. In preferred embodiments, the user input is provided as a verbal command which is received via the microphone 612 and is interpreted into a command via natural language processing. In an example, the user input is provided as a verbal command by a surgeon, "change the speed of the rotary tool to 500 rpm." In some embodiments, the microphone 612 receives instructions from a user of the surgical system. One or more processors of the surgical system of FIG. 6 configure a subset of the surgical tools 154 based on the instructions. For example, in step 1108, the tool control module 628 determines whether the received user input requires an action to be taken. An action can include the changing of a tool parameter or the movement of the robotic arm 604 based on the user input. In an example, a surgeon provides a valid input to "change the speed of the rotary tool to 500 rpm," which is interpreted via natural language processing into a command to execute the actin of setting the rotational speed of the rotary tool to 500 revolutions per minute. In an alternate example, the surgeon requests the operational parameters of the rotary tool by asking, "what is the maximum speed of this tool?" the tool control module 628 determines that this input does not require an action response, but instead a feedback response or reply.

In some embodiments, the surgical robot 602 performs a surgical procedure using a subset of the surgical tools 154 in accordance with a surgical plan. For example, in step 1110, the tool control module 628 enables the action identified from the user input to be performed or executed. The action can include a tool movement, the change of a tool parameter, such as movement or rotational speed, or an instruction for the surgical robot 602's robotic arm 604 to select another end effector 606 which can include a tool, imaging device 616, light, etc. In an example, the tool control module 628 enables the action of setting the rotational speed of the rotary tool to 500 revolutions per minute to be performed.

In some embodiments, the microphone 612 receives a query from a user of the surgical system. The query is directed to at least one parameter of a subset of the surgical tools 154. A speaker (e.g., the speaker 632 of FIG. 6) of the surgical system generates an audible response describing a threshold value. For example, in step 1112, the tool control module 628 provides feedback to the user based on the user's input. The feedback can be via a display screen, indicator light or tone. In a preferred embodiment, the feedback is provided to the user via a synthesized voice in a conversational tone. For example, if a user input is a surgeon requesting the operational parameters of a rotary tool by asking, "what is the maximum speed of this tool?" the feedback response can be, "the maximum speed of this tool is 800 rpm." The feedback can additionally request additional information, such as, "would you like to change the speed?" In step 1114, the tool control module 628 determines whether the user has provided an additional input. The user is determined to have provided an additional input if the user provides another command which can be interpreted into a command via natural language processing. Alternatively, the user can provide an explicit instruction that they have no additional inputs. For example, the surgical robot 602 may ask, "do you need anything else?" to which a surgeon may reply, "no." Alternatively, the surgeon may set down the tool indicating that the surgeon is done with the tool and has no further inputs regarding the tool. In step 1116, the tool control module 628 returns control to the interface module 624. At least one tool having a desired tool configuration is now ready to be used by the surgical robot 602 or a surgeon. In an example, a rotary tool is configured to spin at a speed of 500 revolutions per minute.

The tool control module 628 can perform one or more voice related functions of a surgical system and can verbally notify a user or surgical team of an operational state of one or more of the tools. The tool control module 628 can then receive, via the microphone 612, one or more verbal commands from the surgical team. The surgical system can then control operation of the surgical tool to modify the operational state according to the verbal commands. This allows a user to hear notifications from the surgical system while viewing the surgical procedure. The user can move about the operating room for desired viewing while providing verbally controlling or directing the system. In some embodiments, the surgical system verbally notifies the surgical team of predicted adverse surgical events disclosed herein. The tool control module 628 can verbally provide options for avoiding or mitigating the adverse event. The surgical team can use voice input to select alternatives, modify surgical plans, adjust operational states of one or more tools, or combinations thereof. As discussed below, the tool control module 628 can provide surgical information (e.g., temperatures, positions, sensor measurements, vital signs, etc.) for monitoring the surgical procedure.

Figure 12:
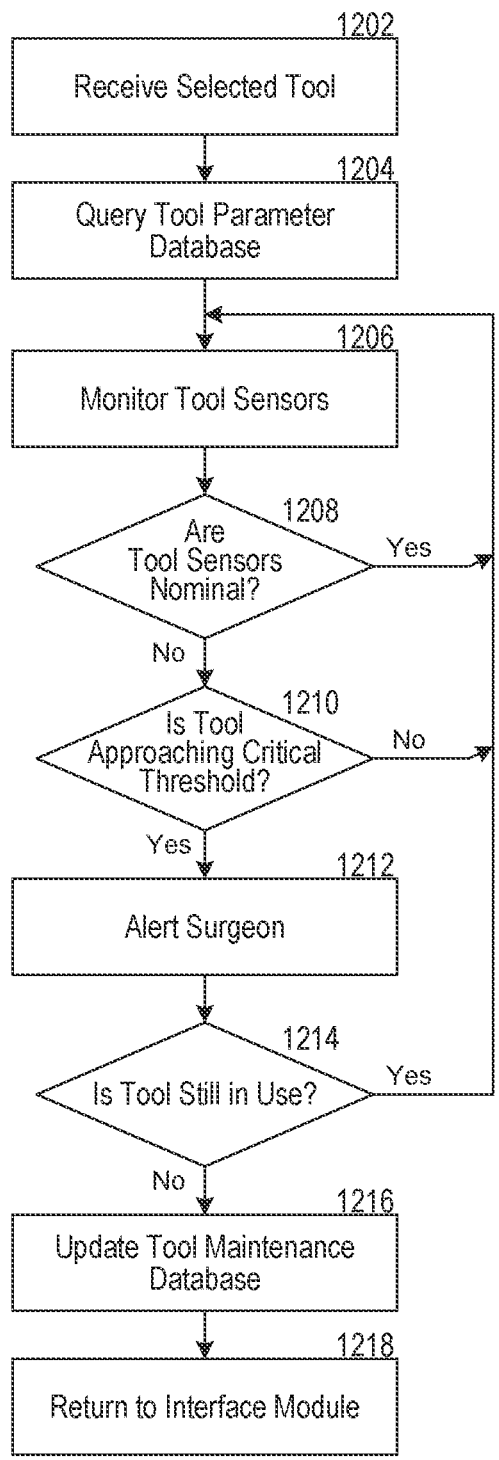
FIG. 12 is a flow diagram illustrating an example process for maintaining and controlling surgical tools, in accordance with one or more embodiments.

FIG. 12 is a flow diagram illustrating an example process for maintaining and controlling surgical tools, in accordance with one or more embodiments. In some embodiments, the process of FIG. 12 is performed by the tool monitoring module 630. The tool monitoring module 630 is illustrated and described in more detail with reference to FIG. 6. In other embodiments, the process of FIG. 12 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1202, the tool monitoring module 630 receives information specifying or describing a tool from the interface module 624. For example, the selected tool is a rotary tool with an operating range of 200-800 revolutions per minute which has been configured by the tool control module 628 to operate at a target speed of 500 revolutions per minute. In step 1204, the tool monitoring module 630 queries the tool parameter database 620 for the tool's operational parameters as specified by the manufacturer. Alternatively, the operational parameters can have been adjusted or otherwise set by the hospital or operating room 102 (see FIG. 1) where the tool is to be used or alternatively a third party who can be responsible for maintenance of the tool. The tool parameters can include minimum and maximum values, such as movement speed, rotational speed, or forces such as gripping, spreading, pushing, or pulling forces. The tool parameter database 620 can additionally include error conditions which can result from a sensor mounted on the tool exceeding a threshold value. Alternatively, an error condition can be triggered by a tool moving into an identified by a tool nearing sensitive tissues which have been identified as a restricted area where the tool should not operate via monitoring by an imaging device 616.

In step 1206, the tool monitoring module 630 monitors at least one sensor affixed to or integrated into the selected tool to monitor a function of the tool or an operational parameter such as operable temperature range, rotational or movement speed, or can monitor safety conditions such as the amount of force applied to the patient, rate of movement or the position of a tool. The sensor can be a force sensor, such as a transducer, a temperature sensor, tachometer, etc. The sensor can alternatively include an imaging device configured to monitor the position and movement of the selected tool and its proximity to nearby tissues and anatomical structures. For example, the sensor is a temperature sensor monitoring the operating temperature of the rotary tool.

In step 1208, the tool monitoring module 630 determines whether the sensors affixed to, integrated into, or oriented toward the tool are indicating nominal operation. Nominal operation indicates that the tool is operating within its intended operational ranges as stored in the tool parameter database 620. The tool sensors can indicate that operation is no longer nominal if they enter a cautionary or warning range which can be a threshold value or a percentage of the operational range. For example, a rotary tool's operating temperature range can be between 40° F. and 140° F. The tool can have a warning threshold set by the manufacturer at 110° F. Alternatively, the warning threshold can be set by the manufacturer as the top 25% of the operational range which in this example would be 115° F. If the tool is operating nominally, no action is necessary.

In step 1210, the tool monitoring module 630 determines whether the tool is approaching the critical threshold for an operational parameter. The critical threshold can be an operating parameter maximum, or a value set by the manufacturer beneath an operating parameter's maximum to prevent reaching the tool's maximum which can result in damage to the tool or harm to a patient or the user. The critical threshold can alternatively be defined by the surgeon and can similarly be set as part of the configuration by the tool control module 628. The critical threshold can be an absolute value or can alternatively be a percentage of the operational range. In an example, the critical threshold is an operating temperature of 135° F. when the maximum operating temperature is 140° F.

In step 1212, the tool monitoring module 630 generates a notification or alerts the user that the operating parameter is approaching a critical threshold as indicated by at least one of the sensors on, in, or oriented toward the tool. The alert can be provided as an indicator light, a notification on a display or an audible tone. In a preferred embodiment, the alert is in the form of a synthesized voice which provides a notification regarding the status of the tool. In an example, the user is a surgeon using a rotary tool which has an internal temperature sensor which is measuring a temperature of 135° F. which is at the critical threshold for the tool and the surgical robot 602 providing a notification to the surgeon, "the tool you are using is about to overheat, please allow the tool to cool before continuing." The surgeon may request additional information, such as, "what is the temperature of the tool?" or "how much longer can I keep using the tool before it damages the tool or harms the patient?" The surgical robot 602 may then provide a response, such as "the tool is currently at 135° F. and its maximum operating temperature is 140° F.," or "The tool is projected to overheat in 30 seconds." The surgeon may then act according to their judgement or may provide an instruction, such as to stop operation of the tool, or may adjust the configuration such as requesting to, "change the rotational speed of the tool to its lowest setting," to extend the operating time without having to stop using the tool.

In step 1214, the tool monitoring module 630 determines whether the tool is still in use. The tool is determined to be still in use if it is still operating. Alternatively, the tool can still be considered in use if it is being held by the user. For example, a surgeon may be assessing the surgical site to gauge their progress but may continue to grasp the tool indicating the tool is still in use. In an alternate embodiment, the rotary tool is still operating indicating that the tool is in use. In another embodiment, the surgeon may have set down the tool or handed the tool to a nurse or other assisting personnel indicating that the tool is no longer in use.

In step 1216, the tool monitoring module 630 updates the tool maintenance database 622 with the usage information. For example, if the tool operated for 5 minutes, the tool monitoring module 630 adds 5 minutes to the cumulative usage time for the tool in the tool maintenance database 622. Alternatively, if maintenance for the tool is based on a number of times the tool is used, the tool monitoring module 630 increments the use counter by one. Additionally, the tool monitoring module 630 updates the tool maintenance database 622 with any issues identified which must be addressed by maintenance. For example, the surgeon may say, "the rotary tool has seized, have it scheduled for maintenance" which may prompt a maintenance event to be scheduled and saved to the tool maintenance database 622. In step 1218, the tool monitoring module 630 returns control to the interface module with a tool status. The tool status can be nominal, not in use, out of service, etc.

The methods discussed in connection with FIGS. 11 and 12 can be used to monitor the usage of subsets of surgical tools over a single surgical procedure or multiple surgical procedures. The surgical systems can generate alerts responsive to determining that one or more of the surgical tools is outside of a target operational range, approaching at least one of an operational limit, reaching an end of service life, etc. The surgical system can modify operational limits and generate a predicted end of service life based on the usage history of the surgical tool, identified wear, and/or servicing. This allows the system to notify the user of potential adverse events with continued usage of the surgical tool. Pre-operative simulations and predictions can be used to notify the surgical team that available surgical tools should not be utilized for future surgical procedures.

The tool monitoring modules disclosed herein can monitor operational states of the tools to provide operating temperatures, operating speeds, energy output, or combinations thereof. The surgical systems can modify operation of the surgical tools to keep operational parameters within acceptable ranges. For example, the operational speed of a surgical tool can be kept within an operational range to keep the operating temperature within an acceptable range. The operating temperature range can be generated by the surgical system, retrieved from a manufacturer, input by a user, or the like. The end of service life can be determined based on, for example, tool usage history, maintenance history, and/or service history. This allows a surgical system to manage inventories for scheduled surgical procedures. Additionally, target operational parameters for tools can vary with usage due to wear. For example, a new rotary tool can have a lower critical threshold rotational speed to provide for an initial break-in to ensure that lubricant is provided evenly through all moving parts. In some embodiments, the break-in procedure enables parts to set against one another. In other embodiments, different types of break-in or run-in procedures are performed to provide for initial wear between components that facilitates desired operation. In some embodiments, the tool monitoring modules disclosed herein can monitor wear characteristics of the tool to determine the end of life.

The surgical systems disclosed herein can analyze scheduled surgical procedures to determine whether the existing inventory includes tools that will remain within operational limits if used in the scheduled surgical procedures. The surgical systems can automatically order additional tools for enabling completion of the scheduled surgical procedures in response to determining insufficient inventory. For example, the system can automatically determine whether the inventory lacks the tools needed to operate within the operational limits. The system can determine confidence scores or levels for tools remaining within operational limits. In some embodiments, the surgical system determines whether a tool will remain within target operational temperatures based on the length of the surgical action, applied load for the surgical action (e.g., abrading, cutting, boring, etc.), or the like.

Surgical plans can be modified based on monitored operational parameters. If operational parameters are reached, the surgical system can modify the surgical plan to complete the surgery while keeping operational parameters within acceptable ranges. In some embodiments, the surgical system can modify an uncompleted portion of a surgical plan to complete the surgical procedure while modifying the operational parameters of the tools, thereby keeping the operational parameters within acceptable ranges. This allows the surgical system to dynamically modify surgical plans based on real-time operational parameters. In some procedures, one or more surgical tools can be replaced with additional surgical tools capable of operating within the planned operational parameters without exceeding critical thresholds.

The functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

We claim:

1. A method comprising:
    receiving, by a surgical system, a surgical plan for a surgical procedure using one or more processors;
    identifying, by the surgical system, surgical tools from a parameter database based on operational parameters in the parameter database corresponding to the surgical plan, wherein the parameter database stores maintenance requirements for the surgical tools;
    determining, by the surgical system, a subset of the surgical tools based on a maintenance status of the subset of the surgical tools retrieved from a maintenance database, wherein the maintenance database stores maintenance history of the surgical tools;
    configuring, by the surgical system, parameters of the subset of the surgical tools based on the operational parameters for performing the surgical procedure, wherein the parameters of the subset of the surgical tools are configurable for intraoperative modification;
    performing, by the surgical system, a first portion of the surgical procedure using a surgical robot and the subset of the surgical tools in accordance with the surgical plan;
    monitoring, by the surgical system, operation of the subset of the surgical tools during the surgical procedure using one or more sensors;
    generating, by the surgical system, an alert responsive to determining that at least one parameter of the parameters of the subset of the surgical tools is approaching a threshold based on the operational parameters in the parameter database; and
    in response to the alert, intraoperatively modifying a second portion of the surgical plan to be performed by:
        determining one or more surgical steps based on at least one surgical goal for a patient;
        selecting a second subset of the surgical tools for performing the one or more surgical steps; and
        determining a new configuration for the subset of the surgical tools based on maintenance records of the subset of the surgical tools and for maintaining the operational parameters within the threshold; and
    intraoperatively modifying, by the surgical system, the subset of the surgical tools to the new configuration by changing a value of the at least one parameter according to the second portion of the surgical plan.

2. The method of claim 1, further comprising:
    querying, by the surgical system, the maintenance database to determine that at least one surgical tool of the subset of the surgical tools requires maintenance; and
    enabling, by the surgical system, maintenance to be performed on the at least one surgical tool to achieve the maintenance status using the parameters in the parameter database.

3. The method of claim 1, further comprising:
    receiving, by the surgical system, instructions from a user of the surgical system using a microphone; and
    performing at least one of:
        adjusting, by the surgical system, the configuring of the subset of the surgical tools based on the instructions; or
        adjusting, by the surgical system, performing of the surgical procedure by controlling the subset of the surgical tools using the surgical robot based on the instructions.

4. The method of claim 1, further comprising:
    determining, by the surgical system, that the surgical procedure is complete responsive to at least one of:
        determining that a tool status of at least one surgical tool of the subset of the surgical tools indicates that the at least one surgical tool is idle; or
        determining that the subset of the surgical tools have been removed from a patient's body based on images received from at least one imaging device of the surgical system.

5. The method of claim 1, further comprising:
    receiving, by the surgical system, a query from a user of the surgical system using a microphone, the query directed to the at least one parameter of the subset of the surgical tools; and
    generating, by the surgical system, an audible response describing the threshold using a speaker.

6. The method of claim 1, wherein the surgical system is voice-controlled, the method further comprising:
    verbally notifying, by the surgical system, an individual of an operational state of at least one of the surgical tools;

receiving, by the surgical system, one or more verbal commands from the individual; and controlling operation of the at least one of the surgical tools to modify the operational state based on the one or more verbal commands.

7. A surgical system comprising:

one or more computer processors; and a non-transitory computer-readable storage medium storing computer instructions, which when executed by the one or more computer processors, cause the surgical system to:

receive a surgical plan for a surgical procedure;

identify surgical tools from a parameter database based on operational parameters in the parameter database corresponding to the surgical plan;

determine a subset of the surgical tools based on a maintenance status of the subset of the surgical tools retrieved from a maintenance database;

configure parameters of the subset of the surgical tools based on the operational parameters for performing the surgical procedure, wherein the parameters of the subset of surgical tools are configurable for intraoperative modification;

perform a first portion of the surgical procedure using the subset of the surgical tools in accordance with the surgical plan using a surgical robot;

monitor operation of the subset of the surgical tools during the surgical procedure using one or more sensors;

generate an alert responsive to determining that at least one parameter of the parameters of the subset of the surgical tools is approaching a threshold based on the operational parameters in the parameter database; and in response to the alert, intraoperatively modifying a second portion of the surgical plan to be performed by:

determining one or more surgical steps based on at least one surgical goal for a patient;

selecting a second subset of the surgical tools for performing the one or more surgical steps; and determining a new configuration for the subset of the surgical tools based on maintenance records of the subset of the surgical tools and for maintaining the operational parameters within the threshold; and intraoperatively modifying the subset of the surgical tools to the new configuration by changing a value of the at least one parameter according to the second portion of the surgical plan.

8. The surgical system of claim 7, wherein the parameter database receives the parameters from a surgical tool manufacturer, and wherein the parameter database stores maintenance requirements for the surgical tools.

9. The surgical system of claim 7, wherein the computer instructions further cause the surgical system to:

query the maintenance database to determine that at least one surgical tool of the subset of the surgical tools requires maintenance; and enable maintenance to be performed on the at least one surgical tool to achieve the maintenance status using the parameters in the parameter database.

10. The surgical system of claim 7, wherein the computer instructions further cause the surgical system to:

receive instructions from a user of the surgical system using a microphone; and perform steps to:

adjust configuring of the subset of the surgical tools based on the instructions; or adjust performing of the surgical procedure by controlling the subset of the surgical tools based on the instructions using the surgical robot.

11. The surgical system of claim 10, wherein the computer instructions to control the subset of the surgical tools cause the surgical system to:

determine a surgical step to be performed by the surgical robot, wherein determining the surgical step is performed using a machine learning model based on the instructions.

12. The surgical system of claim 7, wherein the computer instructions further cause the surgical system to:

determine that the surgical procedure is complete responsive to at least one of:

determining that a tool status of at least one surgical tool of the subset of the surgical tools indicates that the at least one surgical tool is idle; or determining that the subset of the surgical tools have been removed from a patient's body based on images received from at least one imaging device of the surgical system.

13. The surgical system of claim 12, wherein the computer instructions to determine that the subset of the surgical tools have been removed cause the surgical system to:

identify absence of the surgical tools in the patient's body using a machine learning model based on the images.

14. The surgical system of claim 7, wherein the computer instructions further cause the surgical system to:

receive a query from a user of the surgical system using a microphone, the query directed to the at least one parameter of the subset of the surgical tools; and generate an audible response describing the threshold using a speaker.

15. A computer-implemented method comprising:

Identifying surgical tools from a parameter database based on operational parameters in the parameter database corresponding to a surgical plan for a surgical procedure;

determining a subset of the surgical tools based on a maintenance status of the subset of the surgical tools retrieved from a maintenance database; and performing the surgical procedure using a surgical robot and the subset of the surgical tools in accordance with the surgical plan, wherein the surgical tools are configured with the operational parameters;

configuring parameters of the subset of the surgical tools based on the operational parameters for performing the surgical procedure, wherein the parameters of the subset of the surgical tools are configurable for intraoperative modification;

performing a first portion of the surgical procedure using the surgical robot and the subset of the surgical tools in accordance with the surgical plan;

monitoring operation of the subset of the surgical tools during the surgical procedure using one or more sensors;

generating an alert responsive to determining that at least one parameter of the parameters of the subset of the surgical tools is approaching a threshold based on the operational parameters in the parameter database; and in response to the alert, intraoperatively modifying a second portion of the surgical plan to be performed by:

determining one or more surgical steps based on at least one surgical goal for a patient;

selecting a second subset of the surgical tools for performing the one or more surgical steps; and determining a new configuration for the subset of the surgical tools based on maintenance records of the subset of the surgical tools and for maintaining the operational parameters within the threshold; and intraoperatively modifying the subset of the surgical tools to the new configuration by changing a value of the at least one parameter according to the second portion of the surgical plan.

16. The computer-implemented method of claim 15, further comprising:

generating the surgical plan for the surgical procedure using the surgical robot.

17. The computer-implemented method of claim 15, wherein the parameter database stores maintenance requirements for the surgical tools.

18. The computer-implemented method of claim 15, wherein the maintenance database stores maintenance history of the surgical tools.

19. The computer-implemented method of claim 15, further comprising configuring the subset of the surgical tools with the parameters for performing the surgical procedure.

* * * * *